(12) United States Patent
Zhang et al.

(10) Patent No.: US 8,678,555 B1
(45) Date of Patent: Mar. 25, 2014

(54) ENCAPSULATION OF INKJET HEATER CHIP FOR ION BEAM CROSS-SECTION POLISHING AND METHOD OF PREPARING CHIP CROSS-SECTION SAMPLE

(71) Applicant: Funai Electric Co., Ltd., Daito (JP)

(72) Inventors: Qing Zhang, Lexington, KY (US); Xiaoming Wu, Lexington, KY (US)

(73) Assignee: Funai Electric Co., Ltd., Osaka (JP)

(*) Notice: Subject to any disclaimer, the term of this patent is extended or adjusted under 35 U.S.C. 154(b) by 0 days.

(21) Appl. No.: 13/666,062

(22) Filed: Nov. 1, 2012

(51) Int. Cl.
*B41J 2/05* (2006.01)

(52) U.S. Cl.
USPC .................. 347/56; 347/62; 347/63; 347/64

(58) Field of Classification Search
None
See application file for complete search history.

(56) References Cited

U.S. PATENT DOCUMENTS

| | | | |
|---|---|---|---|
| 6,834,937 B2 | 12/2004 | Killmeier | |
| 6,890,062 B2 * | 5/2005 | Bell et al. | 347/56 |
| 7,521,494 B2 | 4/2009 | Choate | |
| 7,571,979 B2 * | 8/2009 | Patil et al. | 347/20 |
| 7,766,455 B2 | 8/2010 | Graham | |
| 8,007,990 B2 | 8/2011 | Patil | |
| 8,163,819 B2 | 4/2012 | Graham | |

* cited by examiner

*Primary Examiner* — Duy Deo
(74) *Attorney, Agent, or Firm* — Amster, Rothstein & Ebenstein LLP

(57) ABSTRACT

A method for preparing an integrated circuit or micro-electro-mechanical system chip sample for ion cross-section polishing is provided. The method includes preparing a polymer coating formulation. The polymer coating formulation includes a novolac epoxy resin, a bisphenol-A/epichlorhydrin epoxy resin, a photoacid generator, an adhesion promoter, and a mixture of acetophenone, cyclohexanone and butyrolactone organic solvents. The integrated circuit or micro-electro-mechanical system chip sample is encapsulated by the polymer coating formulation, wherein the chip sample is then ready for ion beam cross-section polishing. A cross-section sample of integrated circuit or micro-electro-mechanical system chip is prepared by polishing the obtained polymer encapsulated integrated circuit or micro-electro-mechanical system chip with ion beam cross-section polisher. The disclosed method allows the cross-section sample to be obtained at a reduced polishing time. Moreover, a good quality and larger cross-sectional area of the sample is obtained, thus allowing for accurate inspection or analysis of the integrated circuit or micro-electro-mechanical system chip.

18 Claims, 1 Drawing Sheet

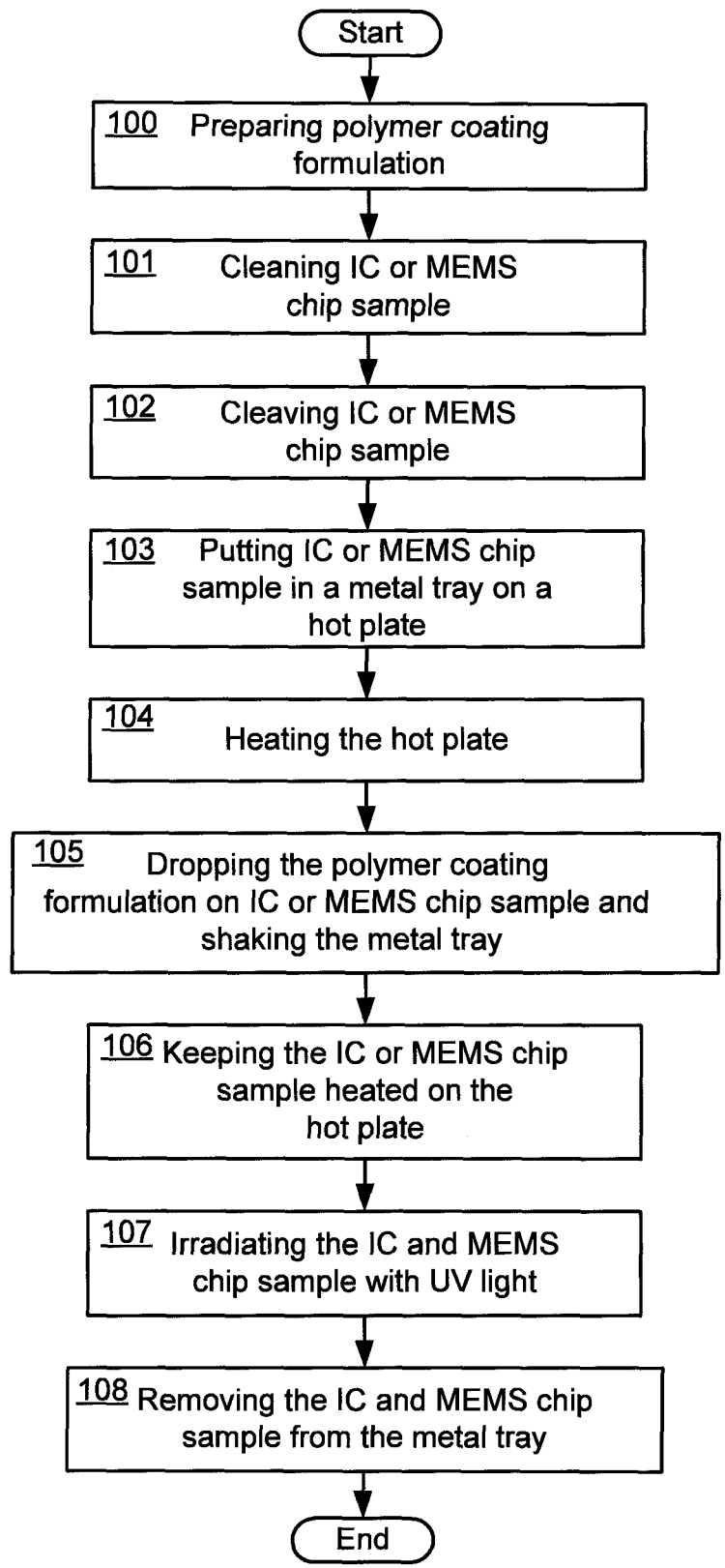

ENCAPSULATION OF INKJET HEATER CHIP FOR ION BEAM CROSS-SECTION POLISHING AND METHOD OF PREPARING CHIP CROSS-SECTION SAMPLE

CROSS REFERENCES TO RELATED APPLICATIONS

This application claims priority to U.S. Provisional Patent Application Ser. No. 61/554,566, filed Nov. 2, 2011, entitled "New Encapsulation formulation for Inkjet Heater Chips and Method for Ion Polishing Cross section," the content of which is hereby incorporated by reference in its entirety.

BACKGROUND

1. Field of the Disclosure

The present disclosure relates to micro-fluid ejection devices, such as inkjet printheads. More particularly, although not exclusively, the disclosure relates to a method of encapsulating an inkjet printhead heater chip for ion beam cross-section polishing. Also disclosed is a method of preparing a cross-section sample of the inkjet printhead heater chip.

2. Description of the Related Art

Thermal inkjet printhead heater chip, also a micro-electro-mechanical system (MEMS) device, is the heart of thermal inkjet technology. Thermal Inkjet technology is a complicated field which requires a delicate, balance of cross disciplines including mechanical engineering, electrical engineering, materials science, chemistry, fluid dynamics, aerodynamics, thermal dynamic and color science.

Thermal inkjet printhead heater chips have a unique construction, consisting of ink vias, hundreds of thin film heaters, ink chambers/nozzle holes, power transistors, logic circuits and contact pads for electrical interconnections. The ink chambers and nozzles are formed by using a thick polymer film having a thickness of 20 to 30 microns. Below the nozzles and ink chambers are thin film heaters, which are about 3 microns thick. During the inkjet heater chip development and ink development, it is important to evaluate the heater chip thin film construction, ink chamber/nozzle construction, heater surface degradation, and ink/heater surface interaction after printing. This evaluation is commonly done by preparing cross-sectional samples of the inkjet heater chip. However, the unique construction of the inkjet heater chip presents a great challenge to preparing quality cross-section samples using typical mechanical polishing and focused ion beam (hereinafter 'FIB') techniques.

Mechanical polishing has been the typical way of preparing cross-section samples for inspection of the thin film profile of inkjet printhead heater chips. Mechanical polishing is abrasive in nature. In protecting the heater chip samples for mechanical polishing, two part epoxy adhesive and a cover glass are traditionally used to encapsulate the heater chips. The two-part epoxy adhesive is an adhesive composition including a first part having an epoxy resin, and a second part having a curing agent. Due to the unique nozzle/chamber structure on top of the thin film heaters, the two-part epoxy adhesive tends to form bubbles at the corners and has poor adhesion to heater surface. The glass/epoxy encapsulation gives enough protection to the polymer nozzle holes and polymer ink chambers, but not enough protection for the thin film stack, as a result, the heater this film stack often delaminates from substrate due to the physical stress during grinding. Such damage deteriorates the interlayer stack of the inkjet heater chip samples and makes it very difficult to accurately measure the thin film thickness. In addition, mechanical polishing also results to rough surfaces which make it impossible to get any identification and measurement of ink build-up or damage on fired heater surface.

In FIB cross-sectioning, inkjet printhead heater chips require a cut that has to be at least 30 microns deep in order to reach the heater thin film stack, so the process is very time consuming. Another problem associated with FIB cross-sectioning of inkjet heaters is the beam damage to heater surface through the open nozzle hole without protective coating. However, depositing platinum as a protective coating is impossible due to the 20 μm to 30 μm deep nozzle. If a polymer protective coating is applied on nozzles, it will be difficult to find the center of the nozzle in FIB using scanning electron microscope, and the process requires even longer cut time.

Because of the problems associated with mechanical polishing and FIB cross-sectioning for sample preparation, ion beam cross-section polishing has been identified as an alternative method for preparing inkjet heater chip cross-section samples. An ion beam cross-section polisher is commercially available from JEOL Ltd, Tokyo, Japan. With ion beam cross-section polishing, the ion beam slowly cuts through the chip, thus a fine cross-section of chip is exposed. Due to the larger ion beam (~150 microns in diameter) of the ion beam cross-section polisher, the sample preparation time is reduced, and the cross-section area is dramatically increased. However, since ion beam polishing uses an ion beam like the FIB, the ion beam still damages the heater surface through the nozzle holes if a protective coating is not applied.

Several materials, such as thin glass cover combined with the two part epoxy adhesive have been tested as coating layers to protect the heater surface from the ion beam damage during the ion beam cross-section polishing. However, due to low ion beam cutting rate of glass, it takes a long time just to cut through the glass cover, so the cost of sample preparation is high when accounting for machine time and mask consumption. The glass cover may be removed, followed by lapping the epoxy adhesive to thin down the protective coating. However, this lapping procedure requires extensive experience and is very time consuming. The glass cover may be replaced with thin silicon to cover the heater chip. The ion beam etches the silicon cover faster than the glass cover, but the non-transparency of the silicon cover to the built-in light microscope in ion beam cross-section polisher makes it difficult to polish a specific area of interest. Other materials such as super glue and a two part epoxy without any cover glass have been tried. However super glue has its limitations, including low viscosity, slow curing, and relatively poor wettability to the heater chip. These limitations result to the super glue not easily staying on the sample surface to provide sufficient protection. A limitation of the two part epoxy is being too viscous to flow into the ink channel to cover the heater surface, resulting in air bubbles and uneven coating.

In preparing the inkjet printhead heater chip samples for ion beam cross-section polishing, it is desired to provide the heater chip with a coating layer that would protect it from damage when exposed to the ion beam. The coating layer needs to have good adhesion to the nozzle plate, the ink flow chamber and the heater surface. Moreover, the coating layer needs to have thin and uniform thickness, be free from voids, and have good mechanical strength and high temperature properties when placed under the ion beam.

Thus, it is desired that the formulation for the coating layer have a rheology that allows it to flow into channels, wet and cover the heater surface, and quick enhancement of the viscosity, thereby allowing the coating layer to stay on top of the heater surface. In addition the formulation for the coating layer has to have a polymer thermal reflow property which allows a process known in the art as "self-healing." Self-healing avoids voids between the coating layer and the heater chip. Furthermore, the coating layer has to have a final cure that provides sufficient mechanical strength.

SUMMARY

The present disclosure provides a method for preparing an integrated circuit, hereinafter (IC), or micro-electro-mechanical system, hereinafter (MEMS), chip sample for ion cross-section polishing. The method includes preparing a polymer coating formulation. The polymer coating formulation includes a novolac epoxy resin, a bisphenol-A/epichlorhydrin epoxy resin, a photoacid generator, an adhesion promoter, and a mixture of acetophenone, cyclohexanone and butyrolactone organic solvents. The novolac epoxy resin has an epoxide equivalent ranging from about 190 to about 250. The bisphenol-A/epichlorhydrin epoxy resin has an epoxide equivalent of greater than about 1000.

The IC or MEMS chip sample is cleaned by removing unnecessary components, cleaved to have the area of interest close to the cutting edge, placed in a metal tray on a hot plate, and heated. In one example embodiment, the method includes dropping the polymer coating formulation onto the heated IC or MEMS chip sample and shaking the metal tray to spread out the polymer coating formulation on channels and surfaces of the IC or MEMS chip sample. The IC or MEMS chip sample are then kept heated on the hot plate to expel voids and remove residual solvents in the polymer coating, and irradiated with an ultraviolet light to cure the polymer coating. A polymer encapsulated IC or MEMS chip sample is then removed from the metal tray, being ready for ion beam cross-section polishing.

In another example embodiment, a cross-section sample of IC or MEMS chip is prepared by polishing the obtained polymer encapsulated IC or MEMS chip with ion beam cross-section polisher. The cross-section sample is obtained at a reduced polishing time with larger cross-section area and in good quality, thus allowing for accurate inspection or analysis of the IC or MEMS chip.

BRIEF DESCRIPTION OF THE DRAWINGS

The accompanying drawings incorporated in and forming a part of the specification, illustrate several aspects of the present disclosure, and together with the description serve to explain the principles of the present disclosure.

FIG. 1 is a flowchart depicting a method for preparing an IC or MEMS chip sample for ion beam cross-section polishing.

DETAILED DESCRIPTION

It is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the terms "a" and "an" herein do not denote a limitation of quantity, but rather denote the presence of at least one of the referenced item.

FIG. 1 illustrates a method of preparing an integrated circuit (IC) or micro-electro-mechanical system (MEMS) chip sample for ion cross-section polishing. The method includes preparing a polymer coating formulation as presented in step 100. The polymer coating formulation includes a novolac epoxy resin, a bisphenol-A/epichlorhydrin epoxy resin, a photoacid generator, an adhesion promoter, and a mixture of acetophenone, cyclohexanone and butyrolactone organic solvents. The novolac epoxy resin has an epoxide equivalent ranging from about 190 to about 250 and is available from Resolution Performance Products of Houston, Tex. under the trade name EPON RESIN SU-8. An "epoxide equivalent" is the number of grams of resin containing 1 gram-equivalent of epoxide. The bisphenol-A/epichlorhydrin epoxy resin has an epoxide equivalent of greater than about 1000 and is available from Shell Chemical Company of Houston, Tex. under the trade name EPON RESIN 1007F. The photoacid generator includes iodonium salt. Suitable example of iodonium salt for use as a photoacid generator includes a mixture of diaryliodonium hexafluoroantimonate-salts, commercially available from the Polyset, Company of Mechanicsville, N.Y. under the trade name PC-2506. The adhesion promoter includes silane. Suitable example of silane for use as an adhesion promoter includes gamma-methacryloxypropyl-tris (2-methoxyethoxy) silane, commercially available from Union Carbide under the trade designation A-175.

In one example embodiment, the polymer coating solution includes about 13.18 percent by weight of novolac epoxy resin, about 13.18 percent by weight of bisphenol-A/epichlorhydrin epoxy resin, about 2.93 percent by weight of photoacid generator, about 0.58 percent by weight of adhesion promoter, about 2.93 percent by weight of butyrolactone solvent, about 17.20 percent by weight of acetophenone solvent, and about 50 percent by weight of cyclohexanone solvent. The polymer coating formulation is prepared by diluting the epoxy resins with the mixture of organic solvents together with the photoacid generator and adhesion promoter.

In step 101, the chip sample is being cleaned. Unnecessary components of the chip sample that are not of interest for analysis is being removed. In one example embodiment, the MEMS chip sample includes an inkjet printhead heater chip. The heater chip is dismantled from the printhead and cleaned to remove ink residue, die-bond, and printhead encapsulation.

In step 102, the chip sample is being cleaved. The cutting edge is placed close to an area of the chip sample that is of interest for inspection or analysis.

In step 103, the cleaved chip sample is placed in a metal tray on a hot plate. In one example embodiment, the metal tray includes an aluminum tray.

In step 104, the chip sample in the metal tray is heated on the hot plate. In one example embodiment, the hot plate is heated at 100° C.

In step 105, the polymer coating formulation is added by drops onto the heated chip sample. The metal tray is then shaken to spread out the polymer coating formulation. The mixture of organic solvents provides the polymer coating solution with good rheology and good wettability on the surface of the chip sample, allowing it to flow through the channels and adhere on the surfaces of the chip sample. As the polymer coating formulation flows, the organic solvent component evaporates while the polymer components lose mobility and adhere on the surface of the chip sample. Cyclohexanone organic solvent, having a lower boiling point than the acetophenone organic solvent, quickly evaporates without creating bubbles in the deposited polymer coating, while acetophenone organic solvent evaporates much slower, thereby maintaining the flowing property of the coating for effectively filling into the channels. In one example embodiment, step 105 is repeated 3 to 5 times.

After step 105, the chip sample is then kept heated on the hot plate for thermal reflow as presented in step 106. This thermal treatment in step 106 removes residual solvents and expels voids at the interface of the formed polymer coating layer on the surface of the chip sample. In one example embodiment, the chip sample is kept on the hot plate at 100° C. for 10 minutes.

In step 107, the thermally treated chip sample is then irradiated with ultraviolet (UV) light to cure the polymer coating layer on the surface of the chip sample. The polymer component crosslinks upon exposure to light, thereby providing the formed coating layer with good mechanical property.

In step 108, the polymer coated chip sample is then removed from the metal tray. Excess polymer coating at the edge and bottom of the chip sample may be cleaned. A polymer encapsulated chip sample is then obtained and ready for on beam cross-section polishing.

The method steps illustrated in FIG. 1 provides a quick and easy way of providing a uniformly thin and strong protective coating on IC or MEMS chip samples in preparation for ion beam cross-section polishing. The IC or MEMS chip samples include, but are not limited to, silicon devices, inkjet printhead heater chip, inkjet printhead contact pins or pads, and gold ball bond on light emitting diode. With the good wettability of the polymer coating solution, the formed protective coating has good adhesion on the surfaces of IC or MEMS chip samples and provides a bubble-free encapsulation. The polymer coating solution is great for encapsulation of chip samples with strong topography such as the inkjet printhead heater chip which includes channels and vias, in addition, the protective coating is transparent to light so the area of interest in the chip sample is visible during ion beam cross-section polishing, thereby allowing for precision cross-sectioning.

In another example embodiment, a cross-section sample of the IC or MEMS chip is prepared by polishing the polymer encapsulated IC or MEMS chip sample obtained by performing step 100 through step 108 illustrated in FIG. 1. The polishing is performed by an ion beam cross-section polisher commercially available from JEOL Ltd, Tokyo, Japan. The polymer coating or encapsulant protects the structure or layers of the IC or MEMS chip sample from on beam damages during polishing. The cross-section sample is then obtained at a reduced polishing time with larger cross-section area and in good quality, thus allowing for accurate inspection or analysis of the IC or MEMS chip.

The foregoing description illustrates various aspects of the present disclosure. It is not intended to be exhaustive. Rather, it is chosen to illustrate the principles of the present disclosure and its practical application to enable one of ordinary skill in the art to utilize the present disclosure, including its various modifications that naturally follow. All modifications and variations are contemplated within the scope of the present disclosure as determined by the appended claims. Relatively apparent modifications include combining one or more features of various embodiments with features of other embodiments.

The invention claimed is:

1. A method for preparing an integrated circuit or micro-electro-mechanical system chip sample for ion beam cross-section polishing, comprising the steps of:
   preparing a polymer coating formulation comprising:
      a novolac epoxy resin having an epoxide equivalent ranging from about 190 to about 250;
      a bisphenol-A/epichlorhydrin epoxy resin having an epoxide equivalent of greater than about 1000;
      a photoacid generator;
      an adhesion promoter; and
      a mixture of organic solvent including acetophenone, cyclohexanone and butyrolactone;
   cleaning the integrated circuit or micro-electro-mechanical system chip sample to remove unnecessary components;
   cleaving the integrated circuit or micro-electro-mechanical system chip sample to have the area of interest close to the cutting edge;
   putting the integrated circuit or micro-electro-mechanical system chip sample in a metal tray on a hot plate;
   heating the hot plate;
   dropping the polymer coating solution onto the integrated circuit or micro-electro-mechanical system chip sample and shaking the metal tray to spread out the polymer coating solution on channels and surfaces of the integrated circuit or micro-electro-mechanical system chip sample;
   keeping the integrated circuit or micro-electro-mechanical system chip sample heated on the hot plate to expel voids and remove residual solvents in the polymer coating;
   irradiating the integrated circuit or micro-electro-mechanical system chip sample with an ultraviolet light to cure the polymer coating; and
   removing the integrated circuit or micro-electro-mechanical system chip sample from the metal tray.

2. The method of claim 1, wherein the polymer coating formulation comprises:
   about 13.18 percent by weight of novolac epoxy resin;
   about 13.18 percent by weight of bisphenol-A/epichlorhydrin epoxy resin;
   about 2.93 percent by weight of photoacid generator;
   about 0.58 percent by weight of adhesion promoter;
   about 2.93 percent by weight of butyrolactone solvent;
   about 17.20 percent by weight of acetophenone solvent; and
   about 50.00 percent by weight of cyclohexanone solvent.

3. The method of claim 1, wherein the metal tray includes an aluminum tray.

4. The method of claim 1, wherein the hot plate is heated at 100° C.

5. The method of claim 1, wherein the dropping of the polymer coating formulation and shaking of the metal tray are repeated 3 to 5 times.

6. The method of claim 1, wherein the integrated circuit or micro-electro-mechanical system chip sample is kept heated on the hot plate at 100° C. for 10 minutes to expel voids and remove residual solvents in the polymer coating.

7. The method of claim 1, wherein the integrated circuit or micro-electro-mechanical system chip sample is irradiated with ultraviolet fight for 10 minutes.

8. The method of claim 1, further including cleaning the excess polymer coating at edges and bottom of the integrated circuit or micro-electro-mechanical system chip sample being removed from the metal tray.

9. The method of claim 1, wherein the micro-electro-mechanical system chip sample is a so heater chip of an inkjet printhead.

10. A method for preparing a cross-section sample of an integrated circuit or micro-electro-mechanical system chip, comprising the steps of:
   preparing a polymer coating formulation comprising:
      a novolac epoxy resin having an epoxide equivalent ranging from about 190 to about 250;
      a bisphenol-A/epichlorhydrin epoxy resin having an epoxide equivalent of greater than about 1000;
      a photoacid generator;

an adhesion promoter; and
a mixture of organic solvent including acetophenone, cyclohexanone and butyrolactone;
cleaning the integrated circuit or micro-electro-mechanical system chip sample to remove unnecessary components;
cleaving the integrated circuit or micro-electro-mechanical system chip sample to have the area of interest close to the cutting edge;
patting the integrated circuit or micro-electro-mechanical system chip sample in a metal tray on a hot plate;
heating the hot plate;
dropping the polymer coating formulation onto the integrated circuit or micro-electro-mechanical system chip sample and shaking the metal tray to spread out the polymer coating formulation on channels and surfaces of the integrated circuit or micro-electro-mechanical system chip sample;
keeping the integrated circuit or micro-electro-mechanical system chip sample heated on the hot plate to expel voids and remove residual solvents in the polymer coating;
irradiating the integrated circuit or micro-electro-mechanical system chip sample with an ultraviolet light to cure the polymer coating;
removing the integrated circuit or micro-electro-mechanical system chip sample from the metal tray; and
performing ion beam cross-section polishing.

11. The method of claim 10, wherein the polymer coating formulation comprises:
about 13.18 percent by weight of novolac epoxy resin;
about 13.18 percent by weight of bisphenol-A/epichlorhydrin epoxy resin;
about 2.93 percent by weight of photoacid generator;
about 0.58 percent by weight of adhesion promoter;
about 2.93 percent by weight of butyrolactone solvent;
about 17.20 percent by weight of acetophenone solvent; and
about 50.00 percent by weight of cyclohexanone solvent.

12. The method of claim 10, wherein the metal tray includes an aluminum tray.

13. The method of claim 10, wherein the hot plate is heated at 100° C.

14. The method of claim 10, wherein the dropping of the polymer coating formulation and shaking of the metal tray are repeated 3 to 5 times.

15. The method of claim 10, wherein the integrated circuit or micro-electro-mechanical system chip sample is kept heated on the hot plate at 100° C. for 10 minutes to expel voids and remove residual solvents in the polymer coating.

16. The method of claim 10, wherein the integrated circuit or micro-electro-mechanical system chip sample is irradiated with ultraviolet light for 10 minutes.

17. The method of claim 10, further including cleaning the excess polymer coating at edges and bottom of the integrated circuit or micro-electro-mechanical chip sample being removed from the metal tray.

18. The method of claim 10, wherein the micro-electro-mechanical system chip sample is a heater chip of an inkjet printhead.

* * * * *